US009384328B1

(12) United States Patent  
Parvizi (10) Patent No.: US 9,384,328 B1  
(45) Date of Patent: Jul. 5, 2016

(54) SYSTEM AND METHOD TO SELECT A PROSTHESIS BASED ON PROXIMAL FEMUR MORPHOLOGY

(71) Applicant: Javad Parvizi, Philadelphia, PA (US)

(72) Inventor: Javad Parvizi, Philadelphia, PA (US)

(73) Assignee: Zimmer, Inc., Warsaw, IN (US)

( * ) Notice: Subject to any disclaimer, the term of this patent is extended or adjusted under 35 U.S.C. 154(b) by 122 days.

(21) Appl. No.: 13/966,322

(22) Filed: Aug. 14, 2013

Related U.S. Application Data (60) Provisional application No. 61/682,866, filed on Aug. 14, 2012.

(51) Int. Cl.
*G06T 7/00* (2006.01)
*G06F 19/00* (2011.01)
*A61B 19/00* (2006.01)

(52) U.S. Cl.
CPC .................................. *G06F 19/345* (2013.01)

(58) Field of Classification Search
None
See application file for complete search history.

(56) References Cited

U.S. PATENT DOCUMENTS

2011/0087465 A1*  4/2011  Mahfouz ........................... 703/1

OTHER PUBLICATIONS

Noble PC, Alexander JW, Lindahl LJ, Yew DT, Granberry WM, and Tullos HS, "The Anatomical Basis of Femoral Component Design," Clin Orthop Relat Res. Oct. 1988;(235):148-65.*
Casper D, Kim G, Parvizi J, and Freeman T, "Femoral Canal Flare Index Displays Medical and Lateral Variation with Age and Gender," 56th Annual Meeting for the Orthopaedic Research Society, Mar. 6-9, 2010.*
Ma R, Xue W, Wang D, Dai K, and Wang C, "Design and manufacture of custom hip prostheses based on standard X-ray films," Int J Adv Manuf Technol 2005(27): pp. 70-74.*

* cited by examiner

*Primary Examiner* — Matthew Bella
*Assistant Examiner* — Soo Shin
(74) *Attorney, Agent, or Firm* — Schwegman Lundberg & Woessner, P.A.

(57) ABSTRACT

Methods and systems for selecting an appropriate prosthesis for a prospective implant recipient are discussed. For example, a method for selecting an appropriate prosthesis can include, accessing anatomical image data, receiving an indication of a plurality of landmark locations within the image data, constructing a femoral canal axial indication within the image data, producing a plurality of lateral anatomic structural measurements, and selecting the appropriate prosthesis to fit the prospective implant recipient. The anatomical image data can include sufficient detail to allow measurement of internal and external geometry of a proximal femur. The plurality of lateral anatomic structural measurements can include measurements along, and perpendicular to, the femoral canal axial indication that run along a femoral canal within the anatomical image data. The prosthesis can be selected based, at least in part, on the plurality of lateral anatomic structural measurements.

18 Claims, 11 Drawing Sheets

SYSTEM AND METHOD TO SELECT A PROSTHESIS BASED ON PROXIMAL FEMUR MORPHOLOGY

CLAIM OF PRIORITY

This application claims the benefit of U.S. Provisional Patent Application Ser. No. 61/682,866, filed on Aug. 14, 2012, the benefit of priority of which is claimed hereby, and is incorporated by reference herein in its entirety.

BACKGROUND

Total hip arthroplasty (THA) is a successful surgical procedure available today. With its continued success, THA is increasingly being offered to an ever growing number of patients, including patients much younger than previously targeted. One of the predictors of a THA outcome is appropriate selection and positioning of the prosthetic components installed. During orthopedic procedures, such as hip replacement surgeries, various tools and instruments are used to assist with prosthetic component selection and placement, including the use of templates as well as provisional or trial implant prosthetics. Despite the various tools currently employed, over-sizing and under-sizing of prosthetic components still occurs. Improper fit can cause long-term fixation and stability issues leading to revision.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Example systems and methods for selecting a prosthesis based on morphology of a proximal femur are described. The systems and methods for selecting a prosthesis, in some examples, provide recommendations based on automated measurements within a medical image of a proximal femur. In the following description, for purposes of explanation, numerous specific details are set forth in order to provide a thorough understanding of example embodiments. It will be evident, however, to one skilled in the art that embodiments of the present invention may be practiced without these specific details. It will also be evident that selection of a prosthesis based on morphology of a proximal femur is not limited to the examples provided and may include other scenarios not specifically discussed. For example, the automated measurement approach discussed herein with respect to a proximal femur can be similarly applied to other implant locations (e.g., distal femur or proximal tibia, among others).

As discussed above, total hip arthroplasty (THA) is considered a successful surgical procedure with a high success rate and a relatively low rate of revision. However, a successful outcome can be heavily dependent on selection of the proper size and shape of prosthetic implant installed. In the case of uncemented THA, it is imperative that a prosthetic stem fit correctly in the proximal femur. Proper fit assures bony ingrowth into the prosthesis, which is important for long-term fixation and stability.

Preoperative templating can be performed in clinical practice to determine the size of femoral stem that is likely to have the best fit characteristics. Preoperative templating can be augmented with intraoperative refinements in making the final selection. Despite these efforts, under-sizing of the stem, leading to lack of osseointegration (or bony ingrowth), or over-sizing, leading to periprosthetic fracture, do occur.

In order to further refine preoperative prosthetic implant selection, the current inventor recognized that various radiographic parameters can be determined for use in clinically selecting the most appropriate femoral implant for a given patient. The radiographic parameters, discussed in more detail below in reference to FIGS. 2A through 2E, can be semi-automatically extracted from radiographic or similar medical images of a patient's proximal femur.

In an example, a physician can use a system, such as system 100 discussed below in reference to FIG. 1, to measure femoral canal dimensions within an anteroposterior (AP) view radiograph. The physician can initiate the process by selecting three landmarks (e.g., points) on the AP view of the patient's proximal femur. In this example, the three points are (i) the midpoint at the isthmus; (ii) the most medial aspect of the lesser trochanter; and (iii) the midpoint of the proximal metaphysic. Once the three landmarks are selected, the system can generate a circle to be positioned over the femoral head. The physician can then center the circle over the femoral head within the AP view radiograph using a user input device connected to the system (e.g., mouse, keyboard, or touch screen, among others). Using the inputs provided by the physician, the system can generate a femoral axis along the length of the femoral canal, and produce a series of measurements at intervals along the femoral axis. In an example, the system can generate measurements every 10 mm starting 20 mm proximal to the lesser trochanter and ending 110 mm distally, resulting in twelve (12) measurements. The measurements can be generated using automated edge detection algorithms. In an example, the edge detection algorithm can be applied based on a difference in pixel density detected on a line drawn out perpendicular to the center point along the femoral axis. This type of automatic image analysis can result in a consistent measurement of the canal border based on radiographic density in a non-subjective manner. In certain examples, the system can provide the option for a manual override to adjust for poor quality radiographs or other anomalies.

In an example, the measurements generated by the system can be used to calculate cortical index (CI), representative of the amount of cortical bone at the isthmus versus the periosteal width at the isthmus. The system can also calculate a canal flare index (CFI), which is representative of the canal width 20 mm proximal to the lesser trochanter versus endosteal width at the isthmus. In some examples, the CFI can be subdivided into a lateral flare index (LFI) and a medial flare index (MFI). The LFI and MFI can be calculated in a fashion similar to the CFI using only the medial or lateral components of the total canal width. These measurements can then be used to select an appropriate prosthetic implant. The system can also determine a desirable stem type from the resulting calculations. For example, a patient with a wide canal (reduced CI and high CFI) may have a cemented femoral stem selected. Patients in the opposite end of the spectrum with type A bone, high CI, and low CFI, may have a modular stem to prevent diaphyseal hang-up and subsequent failure. Other combinations of measurements may result in selection of a tapered metaphyseal stems, a short stem, or a stem with non-proportional metaphyseal to diaphyseal ratios. In certain examples, the system can identify patients with severe deformity and grossly abnormal ration of CI or CFI that may require custom made femoral prosthesis or modular prosthesis.

Example System

Figure 1:
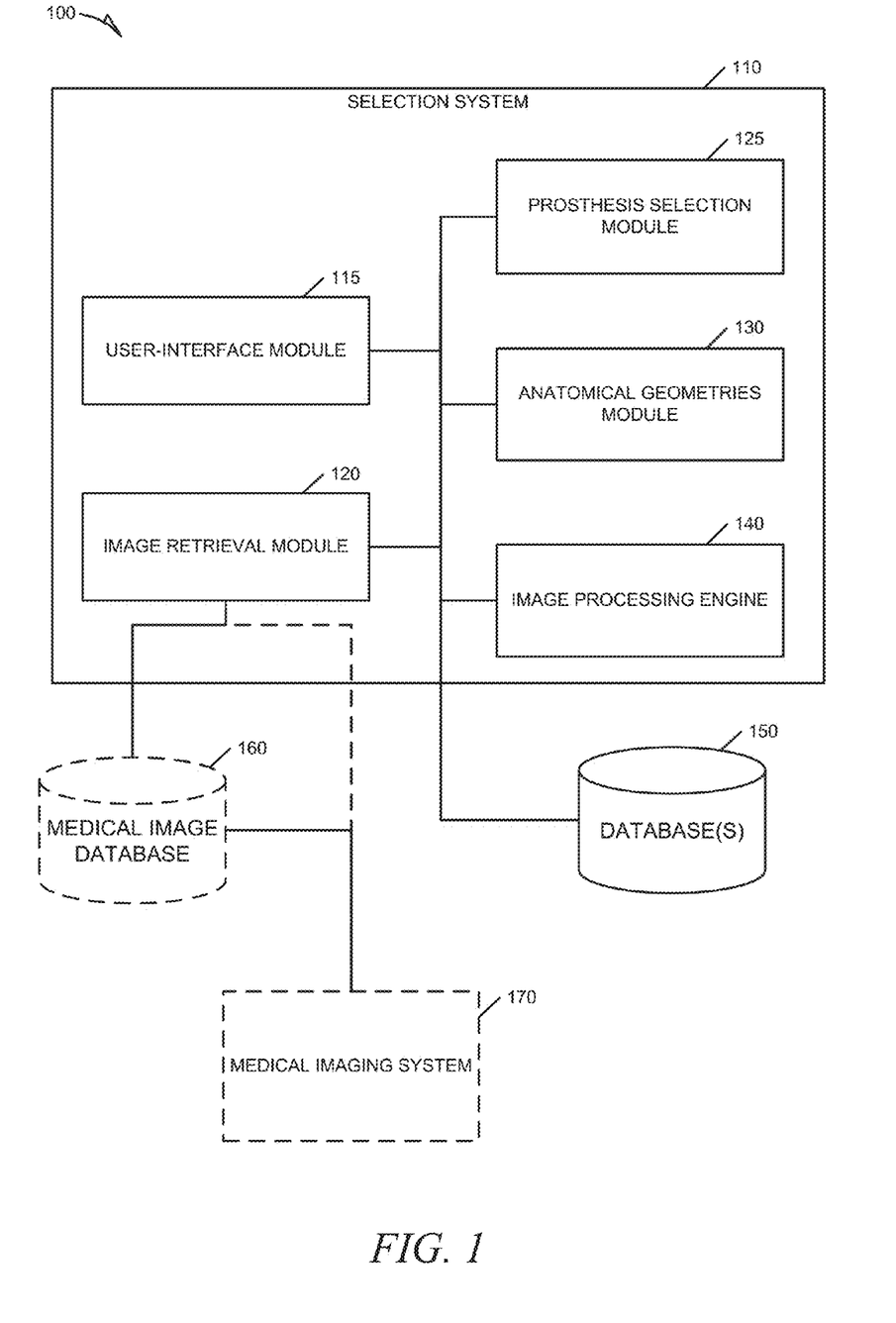
FIG. 1 is a block diagram illustrating a system for selecting a femoral implant based on morphology of a proximal femur, according to an example embodiment.

FIG. 1 is a block diagram illustrating a system 100 for selecting a femoral implant based on morphology of a proximal femur, according to an example embodiment. In this example, the system 100 can include a selection system 110 receiving data from either a medical image database 160 or a medical imaging system 170 and connected to a database 150. In some examples, the selection system 110 can include a user-interface module 115, an image retrieval module 120, a prosthesis selection module 125, an anatomical geometries module 130, and an image processing engine 140.

In an example, the user-interface module 115 can receive input from a physician and provide feedback on the resulting measurements, calculations and prosthesis selection. The user-interface module 115 can process inputs such as the selection of landmarks on a medical image of a proximal femur as well as centering of a region of interest (ROI) around a femoral head within the medial image of the proximal femur. The user-interface module 115 can also process inputs and provide output associated with other aspects of the selection system 110. The user-interface module 115 can interface with user-interface components, such as a display and user-input mechanism (e.g., mouse, keyboard, or touch screen).

In an example, the image retrieval module 120 can retrieve a medical image for processing by the selection system 110 from sources, such as a medical image database 160 or a medical imaging system 170, among others. In some examples, the image retrieval module 120 can communicate directly with medical imaging system 170 to receive a radiographic (or similar) medical image of a patient's proximal femur for processing by the selection system 110. The medical image processed by the selection system 110 can be of any type of medical image that depicts internal structures of a patient's proximal femur. Technologies such as X-Ray, Fluoroscopy, Computerized Tomography, True size imaging (EOS™) and MRI can all produce usable images. Other similar imaging technologies may also be used within the methods and systems discussed herein.

The image processing engine 140 can run various imagine processing algorithms on the medical images retrieved by the image retrieval module 120. The image processing engine 140 can use image processing algorithms such as thresholding, blob analysis, and edge detection, among others, to perform the automated measurements discussed in more detail below in reference to FIGS. 2A through 2E. In an example, the image processing engine 140 can perform measurements using a contrast-based edge detection algorithm. The contrast-based edge detection algorithm functions through detecting a change in contrast within a medical image, such as the change in contrast between different densities of bone. The change in contrast can be plotted and the slope of the line as it crosses a threshold used to further refine the edge detection. In other examples, the image processing engine 140 can implement any known image processing techniques for edge detection and measurement.

In an example, the anatomical geometries module 130 can use measurement data generated by the image processing engine 140 to perform calculations to describe or characterize the geometry of the measured proximal femur. The calculations can include cortical index (CI), canal flare index (CFI), as well as lateral and medial flare indices (MFI, LFI). These calculations are described in further detail below in reference to FIGS. 2A through 2E.

Finally, the prosthesis selection module 125 can use the calculations generated by the anatomical geometries module 130 to select an appropriate prosthetic implant for the particular patient. In an example, the prosthesis selection module 125 can match the various calculation results to dimensions of the available prosthetic implants to optimize fit based on the measured geometries of the patient's proximal femur. In some examples, the prosthesis selection module 125 can look up (e.g., search for) prosthetic implants within database 150, where various prosthetic implants can be stored with associated ranges of applicable calculations for automated selection.

Example Anatomical Measurements and Calculations

Figure 2A:
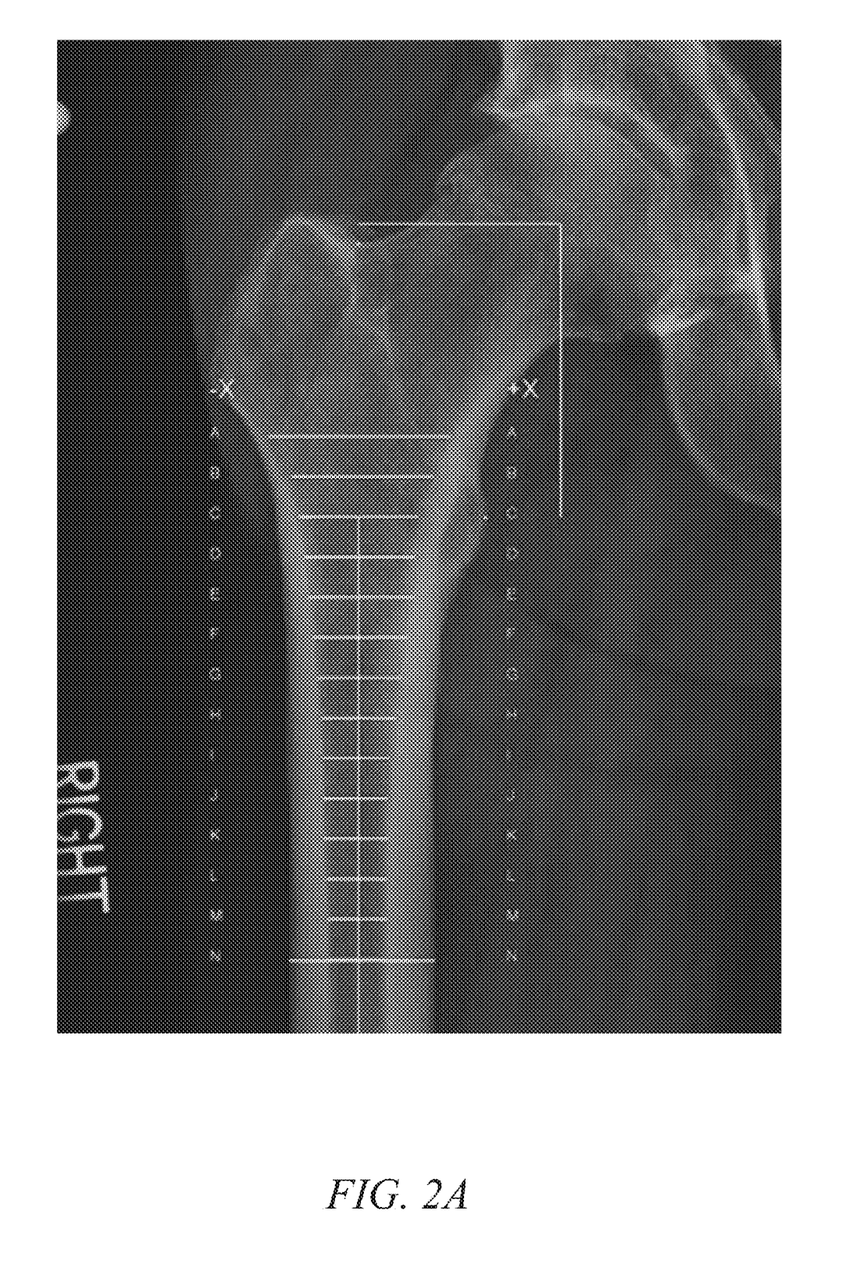
FIG. 2A is a radiograph image illustrating an anteroposterior view of a proximal femur with example measurements indicated, according to an example embodiment.

FIG. 2A is a radiograph image illustrating an anteroposterior (AP) view 200 of a proximal femur with example measurements indicated, according to an example embodiment. In AP view 200, the radiographic image is overlaid with a variety of anatomical measurements that can be performed by the selection system 110. The anatomical measurements within AP view 200 are labeled A through N and categorized as −X and +X. The categorization can reference lateral (−X) versus medial (+X) measurements. The measurements (A-M) illustrated in AP view 200 are measuring the femoral canal at 10 mm intervals, with measurement N measuring the width of the femur at the isthmus.

Figure 2B:
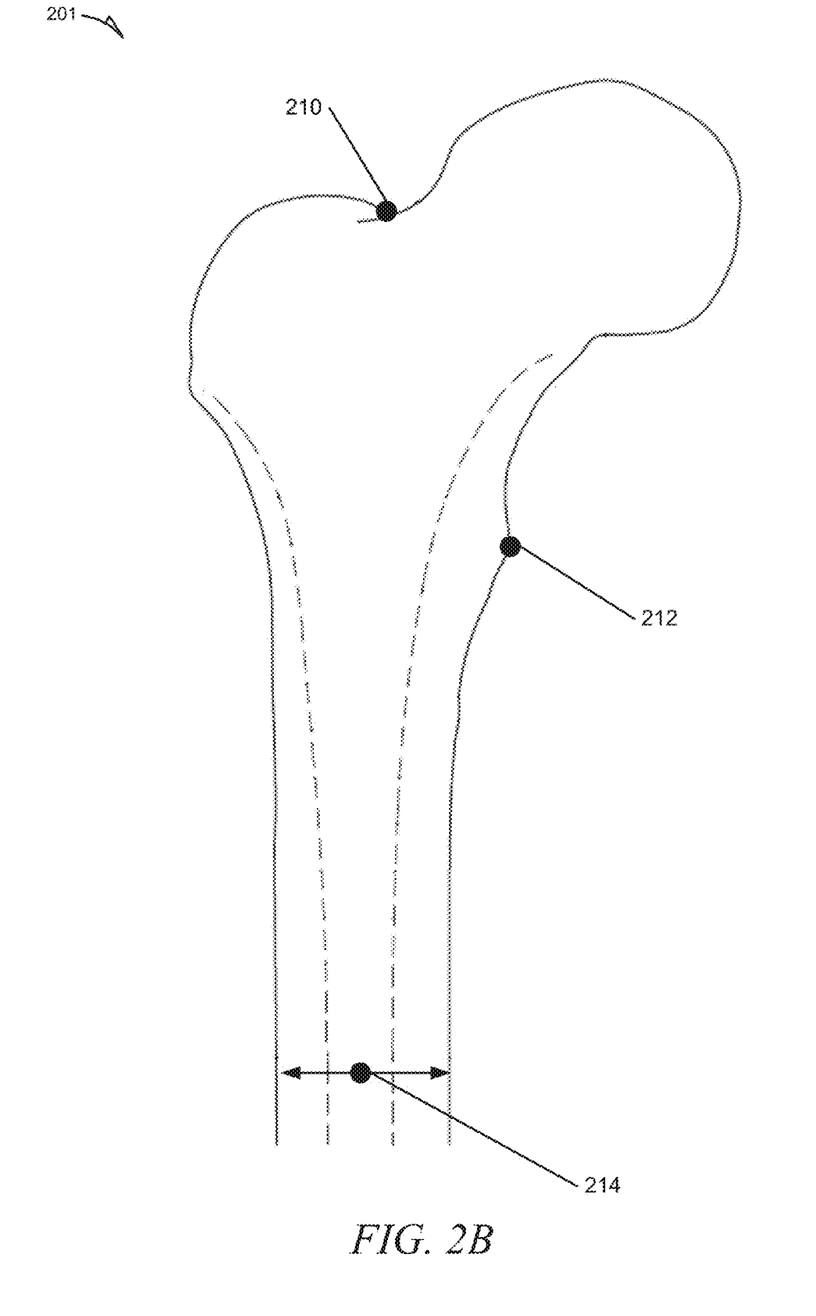
FIG. 2B is a line drawing illustrating an anteroposterior view of a proximal femur with example landmark locations indicated, according to an example embodiment.

FIG. 2B is a line drawing illustrating an anteroposterior (AP) view 201 of a proximal femur with example landmark locations indicated, according to an example embodiment. In an example, the semi-automated process of prosthesis selection can begin with a physician selecting various landmarks within a medical image of a patient's proximal femur. Within AP view 201, three example anatomical landmarks (210, 212, 214) are depicted. In this example, the physician can select the midpoint of the proximal metaphysic (landmark 210), the most medial aspect of the lesser trochanter (landmark 212), and the midpoint at the isthmus (landmark 214) as the anatomical landmarks. The selected landmarks can be used by the selection system 110 to orient subsequent automated measurements and geometry calculations. As illustrated in FIG. 2B, the landmark inputs can be used by the selection system 110 to generate an anatomical axis along the length of the femoral canal and a series of measurements at 10 mm intervals along the anatomical axis. In an example, the measurements can begin 20 mm proximal to the lesser trochanter (landmark 212) and end 110 mm distally at the isthmus (landmark 214). In an example, the measurements can be made from the anatomical axis to the cortex in both the lateral (−X) and medial (+X) directions.

Figure 2C:
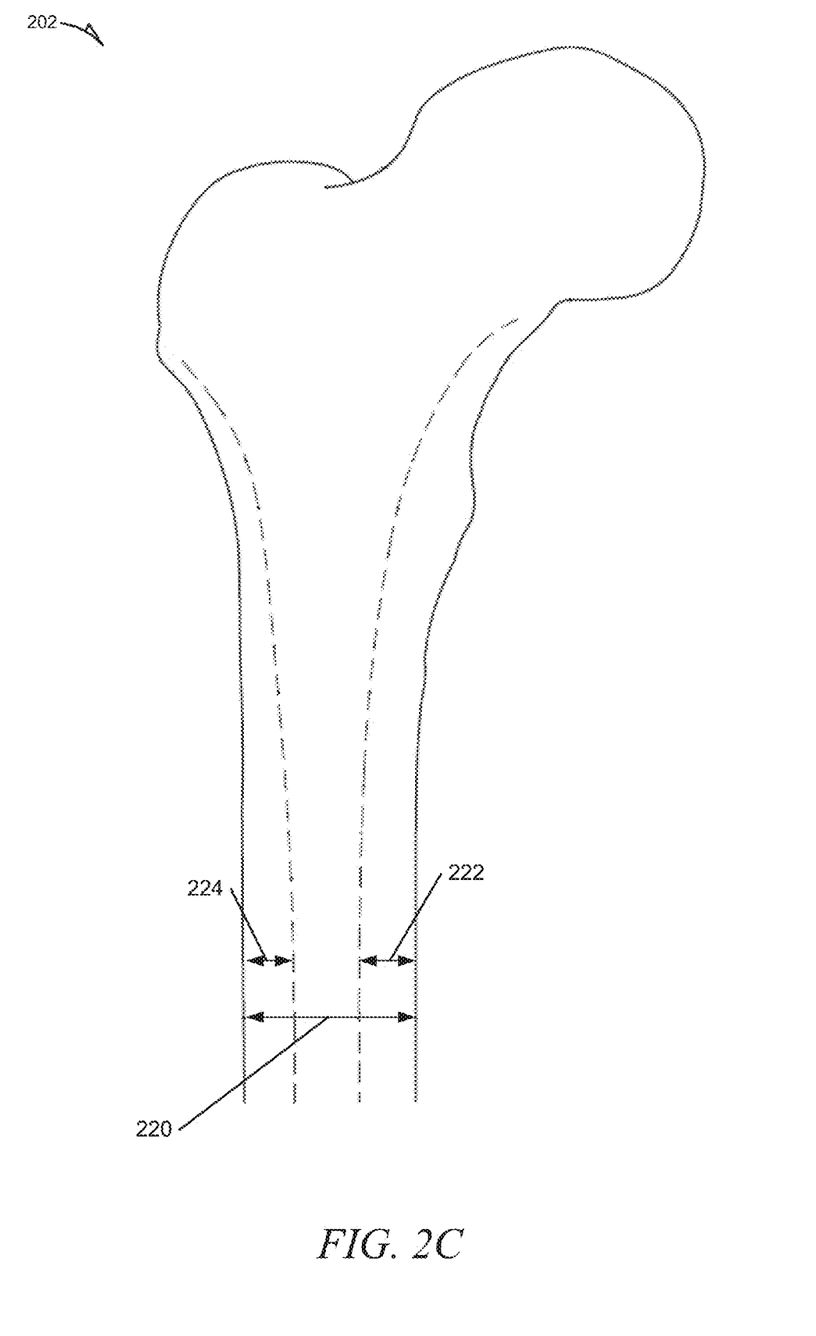
FIG. 2C is a line drawing illustrating an anteroposterior view of a proximal femur with example measurements indicated, according to an example embodiment.

FIG. 2C is a line drawing illustrating an anteroposterior (AP) view 202 of a proximal femur with example measurements indicated, according to an example embodiment. Using automated measurements, such as measurements 220, 222, 224, the selection system 110 can calculate a cortical index (CI). In an example, the CI represents cortical bone thickness measurements at the isthmus (measurements 222, 224) over periosteal width at the isthmus indicated by measurement 220. In this example, the measurements 220, 222, and 224 can be performed at the same level, such as the level of the isthmus indicated by measurement 220. The following formula represents the CI calculation:

$$CI = \frac{222 + 224}{220}$$

Figure 2D:
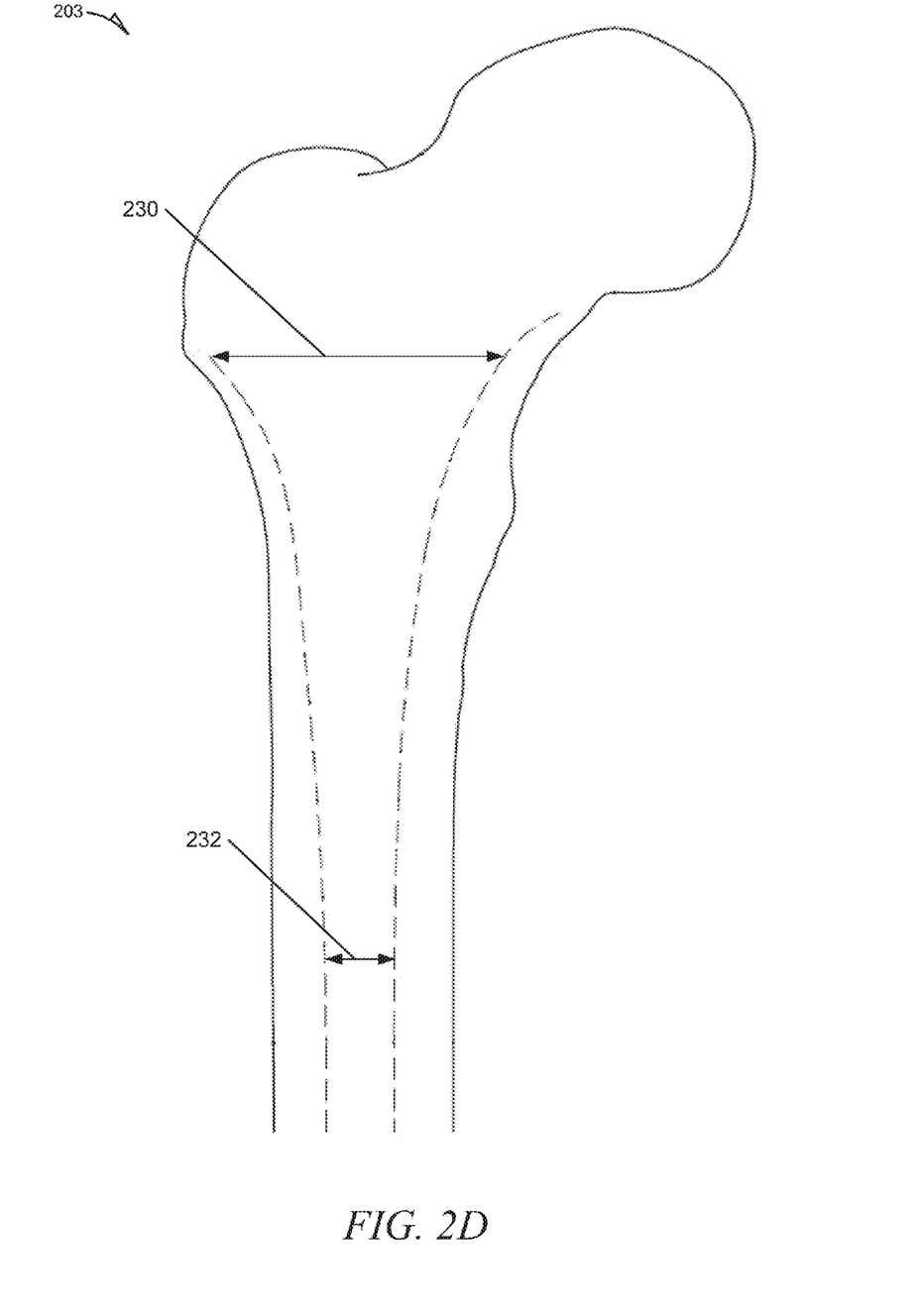
FIG. 2D is a line drawing illustrating an anteroposterior view of a proximal femur with example measurements indicated, according to an example embodiment.

FIG. 2D is a line drawing illustrating an anteroposterior (AP) view 203 of a proximal femur with additional example measurements indicated, according to an example embodiment. Using additional automated measurements, such as measurements 230 and 232, the selection system 110 can calculate a canal flare index (CFI). The CFI can be calculated by taking the measurement of the canal width 20 mm proximal to the lesser trochanter (measurement 230) over the measurement of the endosteal width at the isthmus (measurement 232). The formula for CFI is as follows:

$$CFI = \frac{230}{232}$$

Figure 2E:
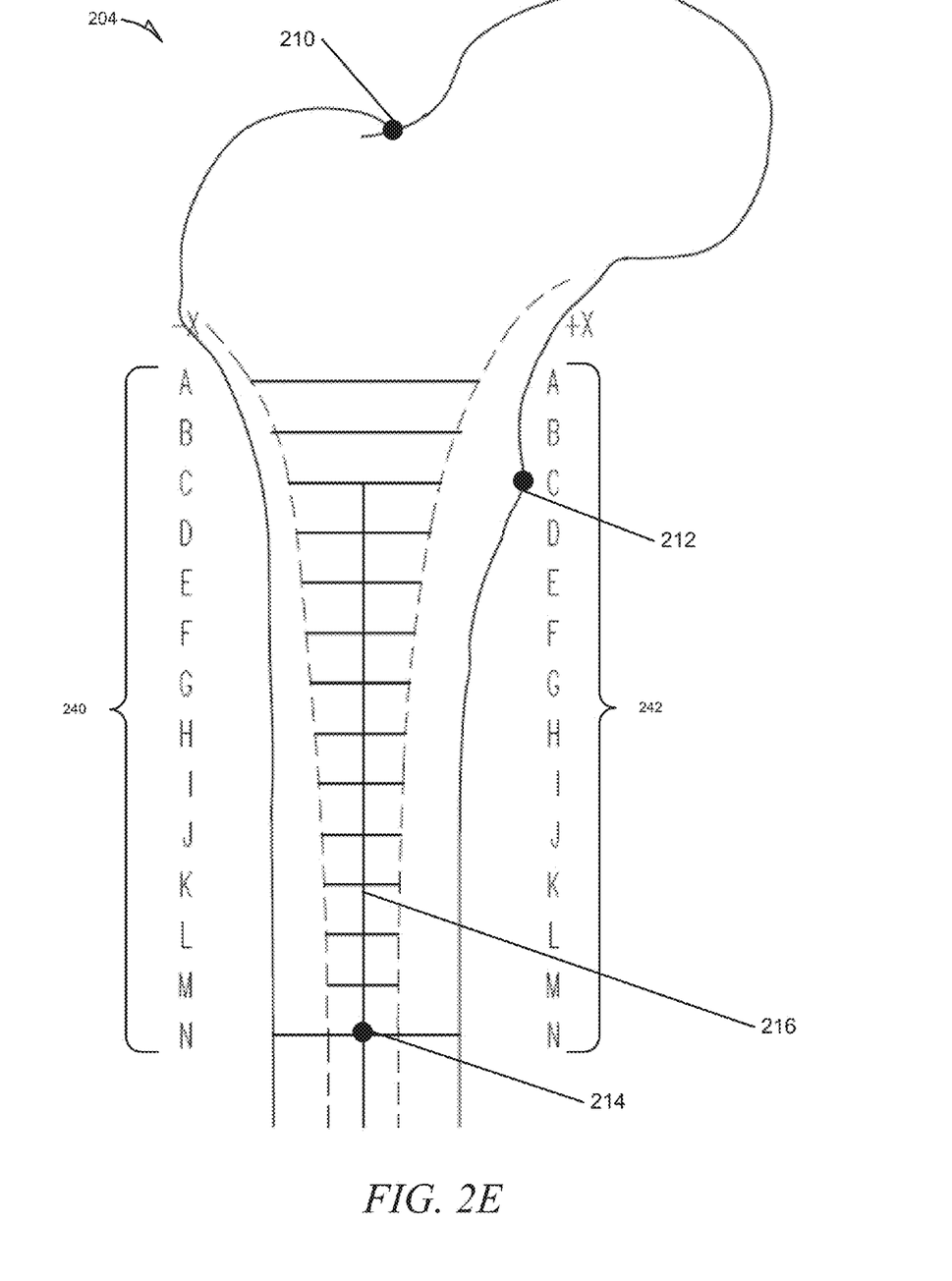
FIG. 2E is a line drawing illustrating an anteroposterior view of a proximal femur with a series of example measurements indicated, according to an example embodiment.

FIG. 2E is a line drawing illustrating an anteroposterior (AP) view 204 of a proximal femur with a series of example measurements indicated, according to an example embodiment. The AP view 204 illustrates another example of a series of measurements (240, 242) along an anatomical axis constructed through the femoral canal (216). The lateral measurements (240) measure from the anatomical axis to the lateral cortical bone at various intervals along the proximal femur. Similarly, the medial measurements (242) measure from the anatomical axis to the medial cortical bone at various intervals along the proximal femur. From these various measurements (240, 242), the selection system 110 can calculate a medial flare index (MFI) and a lateral flare index (LFI) according to the following formulas. Within the following formulas, individual measurements are referenced as [240A], [240B]...[240N] or [214]. Also, all measurements within the following formulas are the absolute value of the measurement, even where the measurement may be in a negative direction within the indicated coordinate system.

$$LFI = \frac{([240A]) + ([214]/2 - ([240N]))}{[214]/2}$$

$$MFI = \frac{([242A]) + ([214]/2 - ([242N]))}{[214]/2}$$

Figure 3A:
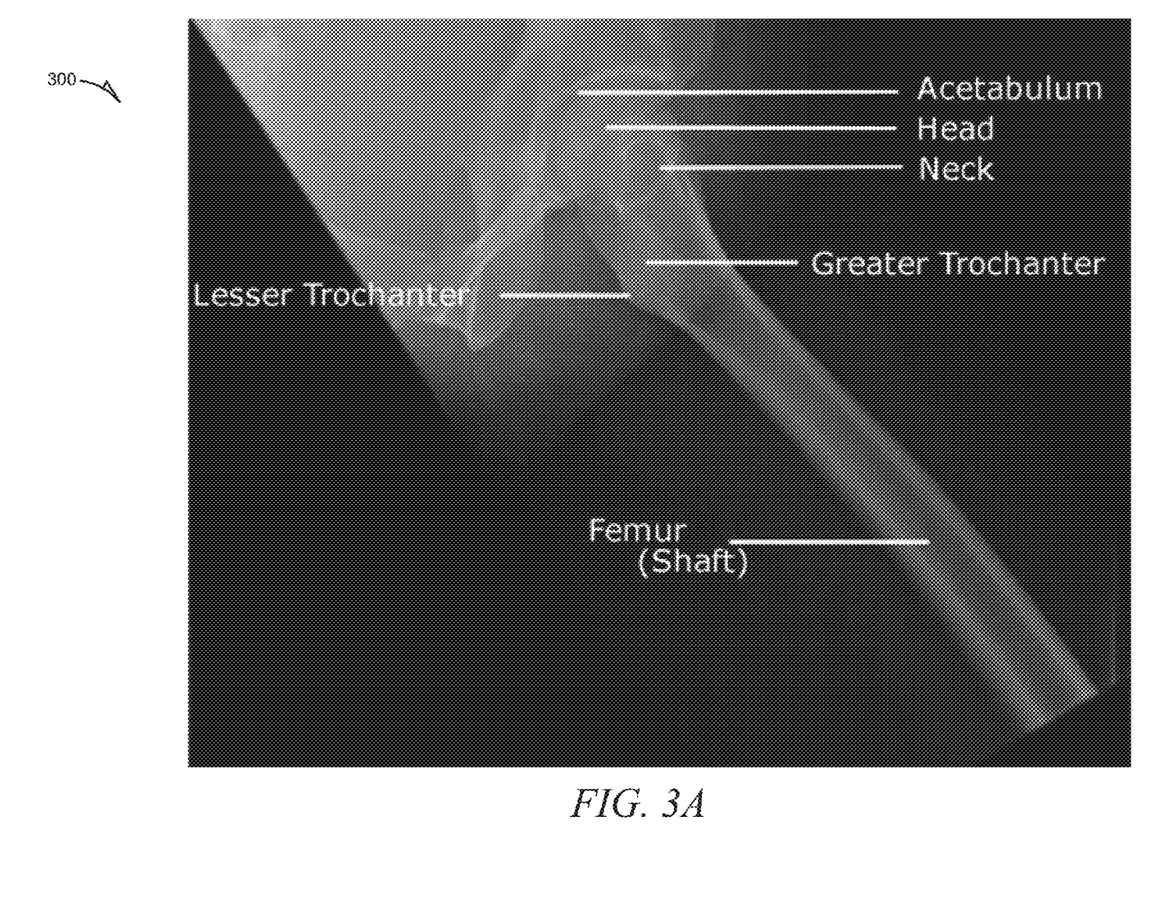
FIG. 3A is a radiograph image illustrating a lateral view of a proximal femur with common proximal femur features indicated, according to an example embodiment.

FIG. 3A is a radiograph image illustrating a lateral view 300 of a proximal femur with common proximal femur features indicated, according to an example embodiment. In some examples, the selection system 110 can generate similar measurements and calculations within a lateral view, such as lateral view 300, of the proximal femur to perform further calculations.

Figure 3B:
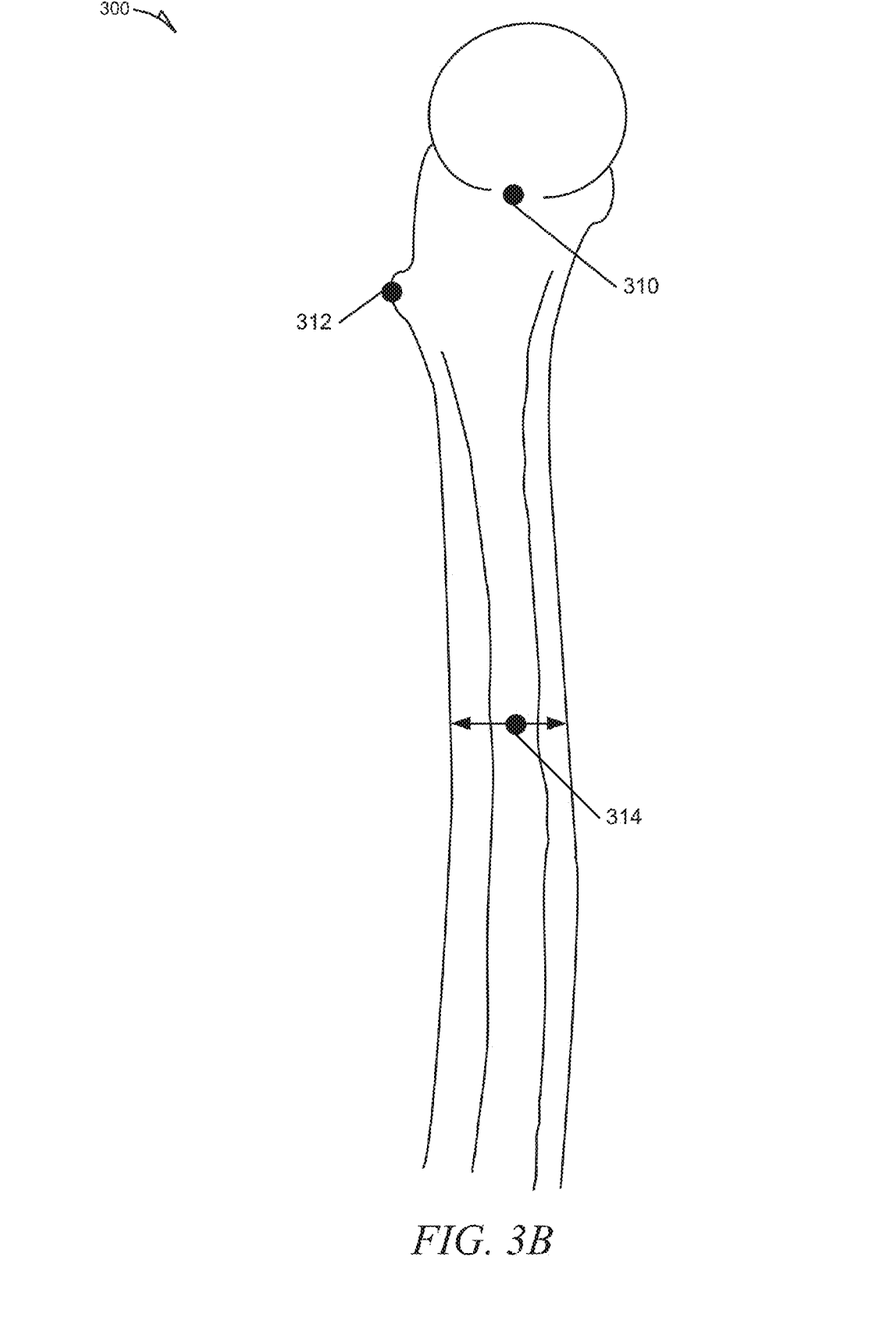
FIG. 3B is a line drawing illustrating a lateral view of a proximal femur with example landmarks indicated, according to an example embodiment.

FIG. 3B is a line drawing illustrating a lateral view 301 of a proximal femur with example landmarks indicated, according to an example embodiment. In an example, the selection system 110 can receive selected landmark locations within a lateral view to assist in automatically deriving certain anatomical geometries, such as version/antiversion of the femoral head. In this example, the physician can select anatomical landmarks, such as the midpoint of the proximal metaphysic (310), the most medial aspect of the lesser trochanter (312), and the midpoint at the isthmus (314). The selection system 110 can subsequently generate a circular region of interest (ROI), which the physician can position over the femoral head. The selection system 110 can combine the AP landmark information with the lateral landmark information, including the AP and later position of the femoral head, to calculate additional anatomical geometries that can be used in selecting an appropriate prosthetic implant.

The following example methods of selecting a prosthesis based on proximal femur morphology are discussed in reference to the measurements and calculations presented above in relation to FIGS. 2A through 2E. However, as mentioned above, similar measurements and calculations can be performed on various other potential implant locations within a human body. For example, similar measurements and calculations could be correlated between a distal femur or proximal tibia and appropriate prosthetic knee implants.

Example Methods

Figure 4:
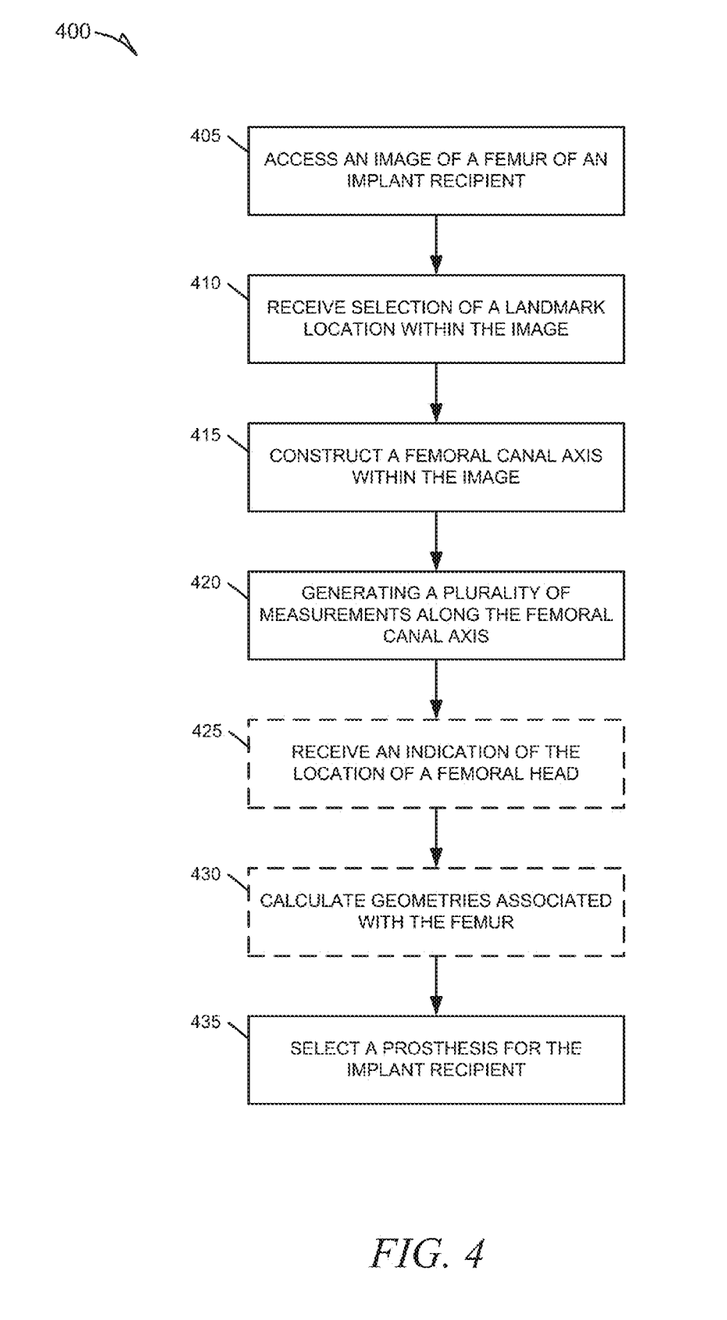
FIG. 4 is a flowchart illustrating a method for selecting a prosthesis based on proximal femur morphology, according to an example embodiment.

FIG. 4 is a flowchart illustrating a method 400 for selecting a prosthesis based on proximal femur morphology, according to an example embodiment. The method 400 can include operations such as: accessing an image at operation 405, receiving selection of landmark locations at operation 410, constructing a femoral canal axis at operation 415, generating a plurality of measurements at operation 420, and selecting a prosthesis at operation 435. Optionally, the method 400 can also include operations such as receiving an indication of the location of a femoral head at operation 425 and calculating geometries associated with the femur at operation 430. The operations associated with method 400 are discussed, primarily, in the order illustrated in FIG. 4. However, the operations discuss can be performed in a different order or in parallel in some examples.

In an example, the method 400 can begin at operation 405 with the selection system 110 accessing an image of a proximal femur of a prospective implant patient. As discussed above, the image can be any radiographic or similar medical image depicting the anatomical structure of the patient's proximal femur. At operation 410, the method 400 can continue with the selection system 110 receiving, via the user-interface module 115, selection of one or more anatomical landmarks within the medical image of the proximal femur. Optionally, the method 400 can process operation 425 with the selection system 110 prompting a physician (or technician) to input an indication of the location of the femoral head of the proximal femur within the image. At operation 425, the method 400 can continue with the selection system 110 receiving indication, such as by placement of an ROI within a user-interface, of the location of the femoral head.

Back at operation 415, the method 400 continues with the selection system 110 constructing an anatomical axis along the femoral canal based at least in part on the landmarks selected in operation 410. At operation 420, the method 400 continues with the selection system 110 generating a plurality of measurements along the anatomical axis constructed along the femoral canal within the image of the patient's proximal femur. Optionally, at operation 430, the method 400 continues with the selection system 110 calculating one or more anatomical geometries associated with the patient's proximal femur. As discussed above, the calculated values can include CI, CFI, MFI, and LFI, among others. Finally, at operation 435 the method 400 can conclude with the selection system 110 selecting a prosthetic implant to best fit the implant recipient. In some examples, the prosthesis selection is based at least in part on the calculated anatomical geometries.

Figure 5:
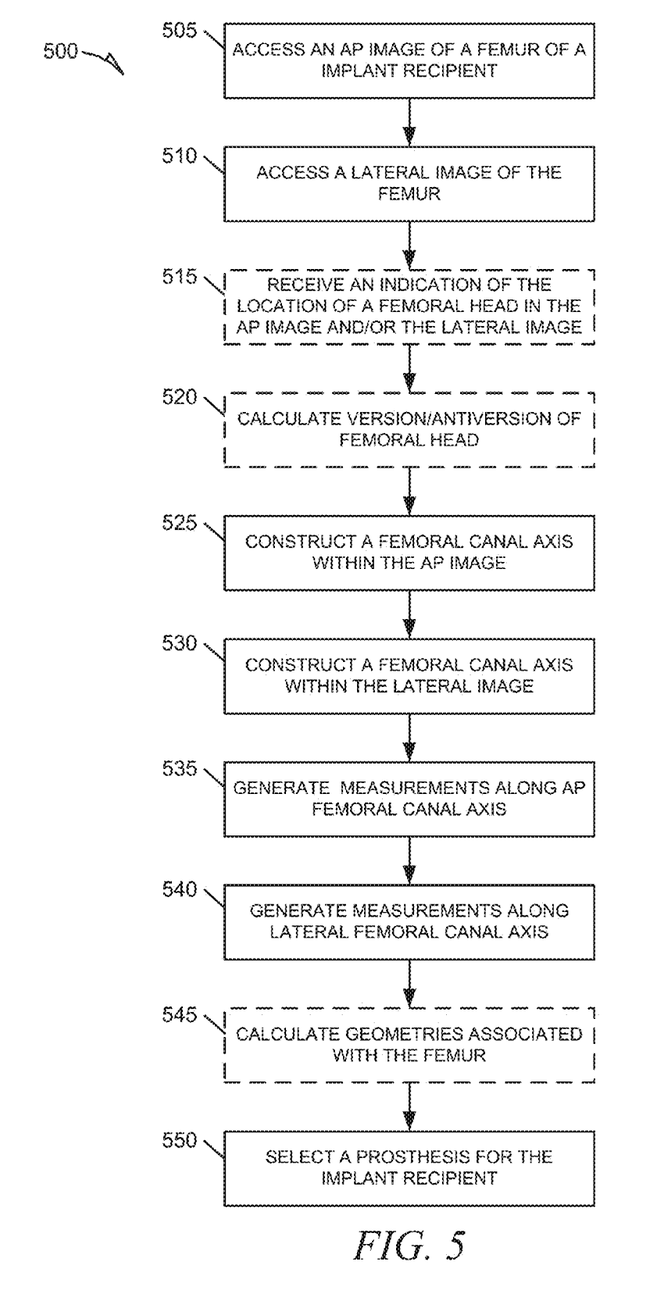
FIG. 5 is a flowchart illustrating a method for selecting a prosthesis based on proximal femur morphology, according to an example embodiment.

FIG. 5 is a flowchart illustrating a method 500 for selecting a prosthesis based on proximal femur morphology, according to an example embodiment. In an example, the method 500 can include operations such as: accessing an AP image at operation 505, accessing a lateral image at operation 510, constructing a femoral canal axis within the AP image at operation 525, constructing a femoral canal axis within the lateral image at operation 530, generating measurements along AP femoral canal axis at operation 535, generating measurements along lateral femoral canal axis at operation 540, and selecting a prosthesis at operation 550. Optionally, the method 500 can also include operations such as: receiving indication of femoral head location(s) at operation 515, calculating version of femoral head at operation 520, and calculating anatomical geometries at operation 545. Similar to method 400, the operations of method 500 are discussed generally in the order illustrated in FIG. 5. However, the operations need not be performed in this order and some may be performed in a different order or in parallel.

In this example, the method 500 can begin at operation 505 with the selection system 110 accessing an AP image of a proximal femur of a prospective implant recipient. At operation 510, the method 500 can continue with the selection system 110 accessing a lateral image of the proximal femur of the prospective implant recipient. Optionally, at operation 515, the method 500 can continue with the selection system 110 receiving an indication of the location of the femoral head within one or both of the AP and lateral images. Obtaining the location of the femoral head in both the lateral and AP images allows the selection system 110 to calculate version or anti-version of the femoral head. Calculating version relies on the AP and lateral images to be taken in known orientation to each other. Accordingly, the method 500 can optionally continue at operation 520 with the selection system 110 calculating version of the femoral head.

At operation 525, the method 500 can continue with the selection system 110 constructing an anatomical axis along the femoral canal within the AP image. At operation 530, the method 500 continues with the selection system 110 constructing an anatomical axis along the femoral canal within the lateral image. With the anatomical axes constructed in both the AP and lateral images, the method 500 can continue at operations 535 and 540 with the selection system generating measurements within both the AP and lateral images along the anatomical axes. Optionally, at operation 545 the method 500 can continue with the selection system 110 calculating anatomical geometries associated with the proximal femur based at least in part on the measurements generated in operations 535 and 540. Finally, at operation 550, the method 500 can conclude with the selection system 110 selecting an appropriate prosthesis for the prospective implant recipient.

Modules, Components and Logic

Certain embodiments are described herein as including logic or a number of components, modules, or mechanisms. Modules may constitute either software modules (e.g., code embodied on a machine-readable medium or in a transmission signal) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation, and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., Application Program Interfaces (APIs).)

Electronic Apparatus and System

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry, e.g., a field programmable gate array (FPGA) or an application-specific integrated circuit (ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Example Machine Architecture and Machine-Readable Medium

Figure 6:
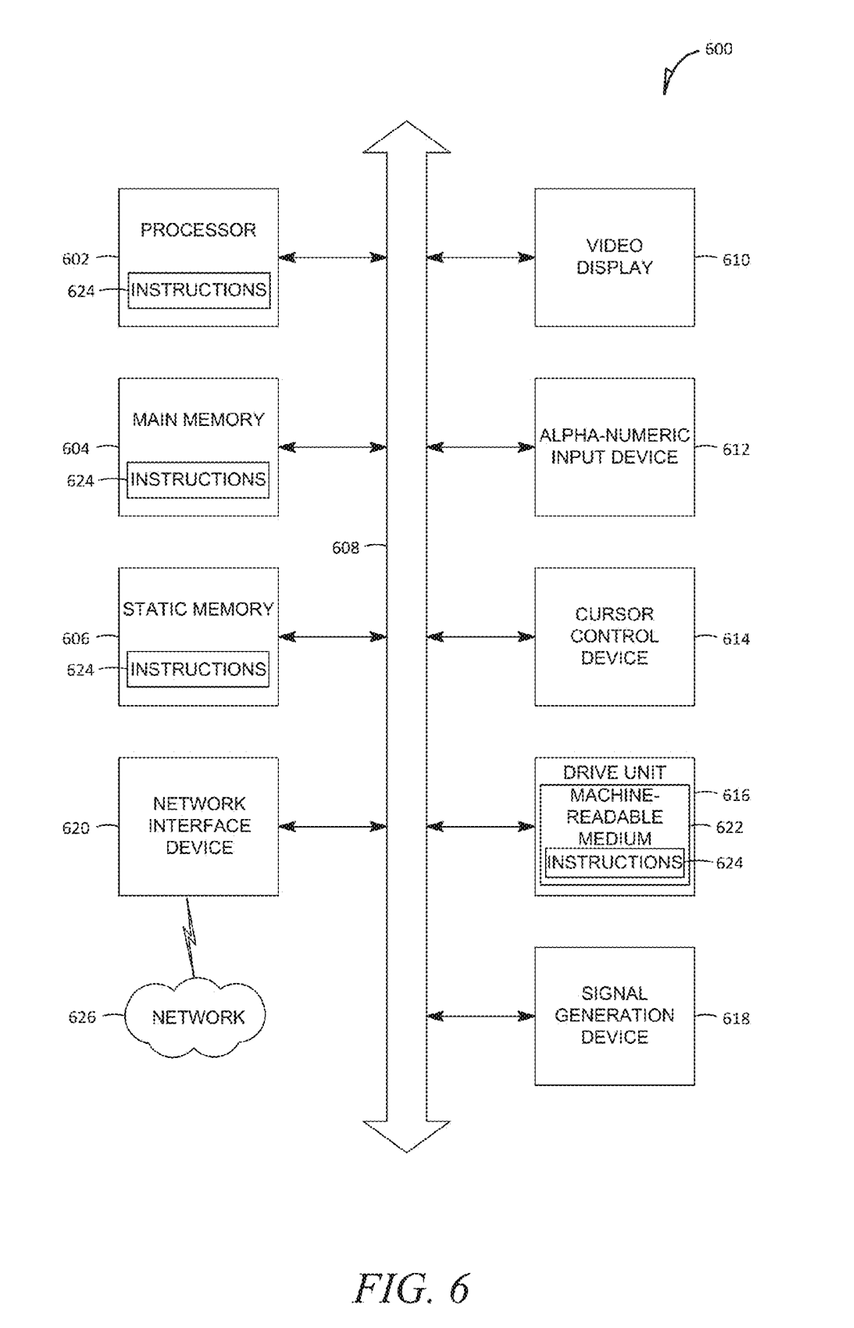
FIG. 6 is a diagrammatic representation of a machine in the example form of a computer system within which a set of instructions for causing the machine to perform any one or more of the methodologies discussed herein may be executed.

FIG. 6 is a block diagram of machine in the example form of a computer system 600 within which instructions, for causing the machine to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 600 includes a processor 602 (e.g., a central processing unit (CPU), a graphics processing unit (GPU) or both), a main memory 604 and a static memory 606, which communicate with each other via a bus 608. The computer system 600 may further include a video display unit 610 (e.g., a liquid crystal display (LCD) or a cathode ray tube (CRT)). The computer system 600 also includes an alphanumeric input device 612 (e.g., a keyboard), a user interface (UI) navigation device 614 (e.g., a mouse), a disk drive unit 616, a signal generation device 618 (e.g., a speaker) and a network interface device 620.

Machine-Readable Medium

The disk drive unit 616 includes a machine-readable medium 622 on which is stored one or more sets of instructions and data structures (e.g., software) 624 embodying or used by any one or more of the methodologies or functions described herein. The instructions 624 may also reside, completely or at least partially, within the main memory 604, static memory 606, and/or within the processor 602 during execution thereof by the computer system 600, the main memory 604 and the processor 602 also constituting machine-readable media.

While the machine-readable medium 622 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures used by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks. "Machine-readable medium," as defined and used within the specification and associated claims, is not intended to include transitory signals, such as those used to wirelessly transmit data between devices.

Transmission Medium

The instructions 624 may further be transmitted or received over a communications network 626 using a transmission medium. The instructions 624 may be transmitted using the network interface device 620 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above detailed description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the detailed description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method comprising:
   accessing anatomical image data including data representing at least a portion of a target orthopedic implant recipient, the anatomical image data including sufficient detail to allow automated measurement of both internal and external geometry of a proximal end of a femur of the target orthopedic implant recipient;
   receiving indication of a plurality of landmark locations within the anatomical image data;
   constructing, based at least in part on the plurality of landmark locations, a femoral canal axial indication along a femoral canal within the anatomical image data;
   producing a plurality of lateral anatomic structural measurements along, and substantially perpendicular to, the femoral canal axial indication, wherein producing the plurality of lateral anatomic structural measurements includes performing at least an edge detection image processing algorithm in multiple locations within at least a portion of the image data using one or more processors to automatically calculate the plurality of lateral anatomic structural measurements;
   calculating, based at least in part on the plurality of lateral anatomic structural measurements, a medial flare index (MFI) and a lateral flare index (LFI); and
   selecting, based at least in part on the plurality of lateral anatomic structural measurements along the femoral canal axial indication, the MFI, and the LFI, a prosthesis from a range of existing prostheses to best fit the femur of the target orthopedic implant recipient.

2. The method of claim 1, wherein receiving indication of the plurality of landmark locations includes receiving a user selection of at least one of:

a midpoint of an isthmus within the femur;
a medial aspect of a lesser trochanter of the femur; and
a midpoint of a proximal metaphysis within the femur.

3. The method of claim 1, wherein receiving indication of the plurality of landmark locations further includes centering a circular region of interest over a femoral head of the femur within the anatomical image data.

4. The method of claim 1, further comprising calculating, based at least in part on the plurality of lateral anatomic structural measurements, a canal flare index (CFI) and a cortical index (CI).

5. The method of claim 4, wherein the selecting the prosthesis is further based on the CFI and the CI calculated from the plurality of lateral anatomic structural measurements.

6. The method of claim 1, wherein the selecting the prosthesis includes calculating a bow in the femur based at least in part on the plurality of lateral anatomic structural measurements and the femoral canal axial indication.

7. The method of claim 1, wherein accessing the anatomical image data includes accessing a radiological image including detail depicting the femoral canal.

8. The method of claim 1, wherein accessing the anatomical image data includes accessing a medical image depicting an anteroposterior view of a pelvic region of the target implant recipient.

9. The method of claim 1, wherein performing the edge detection image processing algorithm includes detecting a change in contrast within the anatomical image data representing a change in bone density and using a predetermined threshold to select an edge.

10. A system comprising:
a computer including at least one processor and a memory device, the memory device including instructions that, when executed by the at least one processor, cause the computer to:
access anatomical image data including data representing at least a portion of a target implant recipient, the anatomical image data including sufficient detail to enable automated measurement of both internal and external geometry of a proximal end of a femur of the target implant recipient;
receive selection of a plurality of landmark locations within the image data;
construct, based at least in part on the plurality of landmark locations, a femoral canal axial indication along a femoral canal within the image data;
produce a plurality of anatomic structural measurements using at least an edge detection image processing algorithm, operating on the at least one processor, in multiple locations within at least a portion of the image data to automatically calculate the plurality of anatomic structural measurements along, and substantially perpendicular to, the femoral canal axial indication;
calculate, based at least in part on the plurality of lateral anatomic structural measurements, a medial flare index (MFI) and a lateral flare index (LFI); and
select, based at least in part on the plurality of lateral anatomic structural measurements along the femoral canal axial indication, the MFI, and the LFI, a prosthesis from a range of existing prostheses to best fit the femur of the target orthopedic implant recipient.

11. The system of claim 10, wherein the instructions that cause the computer to receive selection of the plurality of landmark locations further include instructions that cause the computer to receive selection of at least one of:
a midpoint of an isthmus within the femur;
a medial aspect of a lesser trochanter of the femur; and
a midpoint of a proximal metaphysis within the femur.

12. The system of claim 10, wherein the instructions that cause the computer to receive selection of the plurality of landmark locations further include instructions that cause the computer to receive input centering a circular region of interest over a femoral head of the femur within the anatomical image data.

13. The system of claim 10, wherein the instructions further include instructions that cause the computer to calculate, based at least in part on the plurality of anatomic structural measurements, a canal flare index (CFI) and a cortical index (CI); and
wherein the instructions that cause the computer to select the prosthesis further include instructions that cause the computer to select the prosthesis based at least in part on the CFI and the CI calculated from the plurality of anatomic structural measurements.

14. The system of claim 10, wherein the instructions that cause the computer to access the image data further include instructions to cause the computer to access a radiological image including detail depicting the femoral canal.

15. The system of claim 10, wherein the instructions that cause the computer to access the image data further include instructions to cause the computer to access a medical image depicting an anteroposterior view of a pelvic region of the target implant recipient.

16. A machine-readable storage device including instructions that, when executed by a machine, cause the machine to:
access a first anatomical image of at least a portion of a target implant recipient, the first anatomical image depicting an anteroposterior view of external and internal geometry of a proximal end of a femur of the target implant recipient;
construct, within the first anatomical image, a femoral canal axial indication along a femoral canal of the femur;
produce a first plurality of anatomical structural measurements along, and substantially perpendicular to, the femoral canal axial indication within the first anatomical image, wherein producing the plurality of lateral anatomic structural measurements includes instructions to perform at least an edge detection image processing algorithm in multiple locations within at least a portion of the image data to automatically calculate the plurality of lateral anatomic structural measurements; and
calculate, based at least in part on the first plurality of lateral anatomic structural measurements, a medial flare index (MFI) and a lateral flare index (LFI); and
select, based at least in part on the first plurality of anatomical structural measurements, the MFI, and the LFI, a prosthesis from a set of existing prostheses to best fit the femur of the target implant recipient.

17. The machine-readable storage device of claim 16, further including instructions that cause the machine to:
calculate a second plurality of anatomical structural measurements within the first anatomical image, the second plurality of anatomical structural measurements associated with a femoral head of the femur;
access a second anatomical image of the portion of the target implant recipient, the second anatomical image depicting a lateral view of external and internal geometry of the proximal end of the femur of the target implant recipient;
calculate a third plurality of anatomical structural measurements within the second anatomical image, the third plurality of anatomical structural measurements associated with the femoral head of the femur; and wherein the instructions that cause the machine to select the prosthesis further include instructions that cause the machine to calculate a version of the femoral head based at least in part on the second plurality of anatomical structural measurements and the third plurality of anatomical structural measurements.

18. The machine-readable storage device of claim 16, wherein the instructions further include instructions that cause the machine to:

produce a fourth plurality of anatomical structural measurements along, and substantially perpendicular to, a femoral canal axial indication within the second anatomical image;

calculate, based at least in part on the first plurality of anatomical structural measurements and the fourth plurality of anatomical structural measurements, a canal flare index (CFI) and a cortical index (CI); and wherein the instructions that cause the machine to select the prosthesis further include instructions that cause the machine to select the prosthesis based at least in part on the CFI and the CI.

* * * * *